United States Patent [19]

Luloff et al.

[11] 3,959,276

[45] May 25, 1976

[54] ANTIBACTERIAL PRODUCT

[75] Inventors: Jerome S. Luloff, Bloomington, Minn.; Albert L. Eilender, Flanders, N.J.

[73] Assignee: Cosan Chemical Corporation, Clifton, N.J.

[22] Filed: Nov. 26, 1974

[21] Appl. No.: 527,364

Related U.S. Application Data

[62] Division of Ser. No. 403,819, Oct. 5, 1973.

[52] U.S. Cl. ............................ 260/248.5; 424/249
[51] Int. Cl.$^2$ ..................................... C07D 251/04
[58] Field of Search .................................. 260/248.5

[56] References Cited
UNITED STATES PATENTS

| | | | |
|---|---|---|---|
| 3,758,464 | 9/1973 | Prindle et al. | 260/248.5 |
| 3,784,529 | 1/1974 | Bayer et al. | 260/248.5 |

*Primary Examiner*—John M. Ford
*Attorney, Agent, or Firm*—Pennie & Edmonds

[57] ABSTRACT

A number of water-soluble, one-to-one quaternary ammonium adducts of unsaturated organic halides and dihalides with hexamethylenetetramine are known as being useful as antimicrobial agents. It has now been discovered that a two-to-one quaternary ammonium adduct can be prepared from hexamethylenetetramine and 3,4-dichlorobutene-1; this two-to-one adduct is a more active, less toxic antimicrobial agent than the known one-to-one quaternary ammonium adducts.

2 Claims, No Drawings

ANTIBACTERIAL PRODUCT

This is a division of application Ser. No. 403,819, filed Oct. 5, 1973.

BACKGROUND OF THE INVENTION

During 1915 and 1917 a number of papers were published by Dr. Walter Jacobs and coworkers at the Rockefeller Institute for Medical Research describing the general bactericidal character of quaternary ammonium salts of hexamethylenetetramine. The bactericidal activity of these compounds was primarily attributed to the presence of the hexamethylenetetramine nucleus; however, the degree or extent of this activity was said to be determined by the nature of the molecular groups adducted with the hexamethylenetetramine. The principal mode of action of these quaternary ammonium salts of hexamethylenetetramine was said to be the controlled, regulated decomposition of the hexamethylenetetramine nucleus to liberate formaldehyde. The following group of papers by Jacobs and coworkers are of interest in this regard: *Proc. Nat. Acad. Sci. U.S.A.*, 1, 226 (1915); *J. Biol. Chem.*, 20, 659 (1915); *J. Biol. Chem.*, 21, 465 (1915); *J. Exp. Med.*, 24, 563 (1916); and *J. Exp. Med.*, 25, 363 (1917). These Jacobs papers, however, do not describe any quaternary ammonium adducts of hexamethylenetetramine with unsaturated acyclic dihalides.

In U.S. Pat. No. 3,228,829 Wolf and a coworker at the Dow Chemical Company have more recently described as antimicrobial agents a group of one-to-one quaternary ammonium adducts of hexamethylenetetramine with unsaturated halides and dihalides. Among the useful unsaturated halides and dihalides described are the dihaloalkenes and haloalkynes, specifically 1,3-dichloropropene.

In French Pat. No. 1,363,240 Frank and coworkers at Farbenfabriken Bayer even more recently described as antibacterial agents a group of one-to-one quaternary ammonium adducts of hexamethylenetetramine with α,ω-dihalogenated hydrocarbons. Among the group of useful α,ω-dihalogenated hydrocarbons described is 1,4-dichlorobutene-2.

We have now discovered that a two-to-one quaternary ammonium adduct can unexpectedly be prepared by reacting hexamethylenetetramine with 3,4-dichlorobutene-1. Moreover, this two-to-one quaternary ammonium adduct is more active and less toxic than the one-to-one adducts described by both Wolf and Frank and consequently is significantly more advantageous as an antimicrobial agent, particularly from a safety and environmental standpoint.

BASIC PARAMETERS OF THE INVENTION

A. Preparation of the Product

When hexamethylenetetramine and the dihalides of Wolf and Frank react, only one of the halogens is displaced by hexamethylenetetramine to form a quaternary ammonium salt. The second halogen, however, is unreactive and, therefore, only a one-to-one quaternary ammonium adduct is formd. On the contrary, when hexamethylenetetramine and 3,4-dichlorobutene-1 react, both chlorines are displaced by the hexamethylenetetramine so that a two-to-one quaternary ammonium adduct is formed.

Contrary to the reaction of the Wolf and Frank dihalides, it is believed that the reaction of this invention between hexamethylenetetramine and 3,4-dichlorobutene-1 proceeds by a rearrangement mechanism which results in the presence during the reaction of two reactive sites on the dihalide and thus allows for the preparation of the two-to-one rather than the one-to-one quaternary ammonium adduct. The reaction is believed to occur in the following fashion, with the rearrangement being accomplished by the allylic displacement of the 3-chlorine and concomitant shift of the double bond:

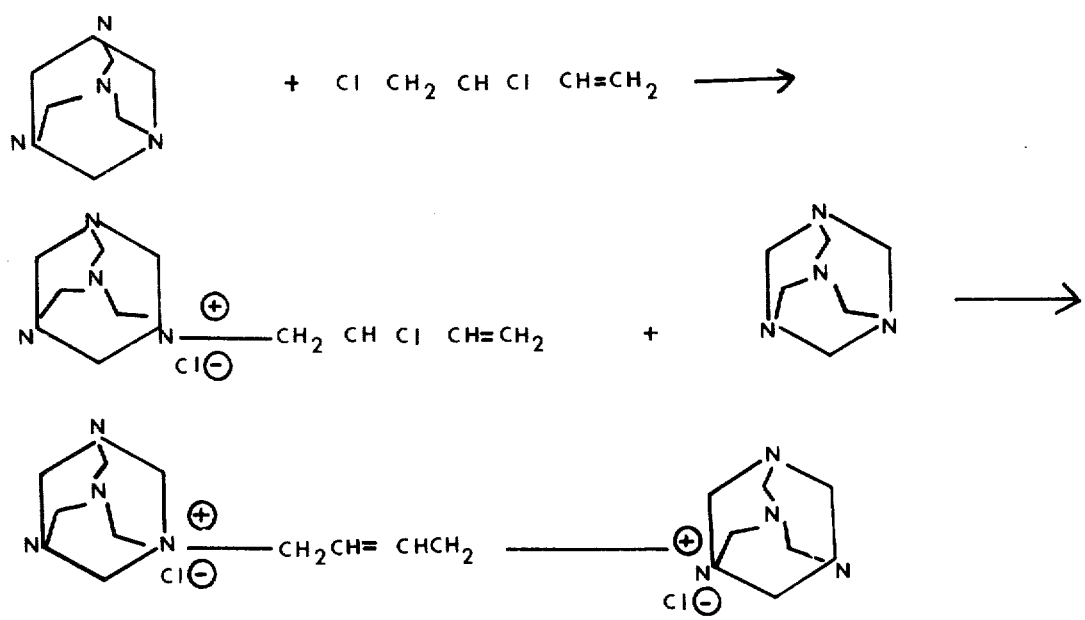

Regardless of the actual mechanism of the reaction, the analytical data available on the product clearly indicate that the two-to-one quaternary ammonium adduct is formed. Particularly, the analyses for percent ionic chlorine and percent nitrogen in the final product indicate that the two-to-one quaternary ammonium adduct is obtained according to this invention. Moreover, nuclear magnetic resonance and infrared data indicate the product is symmetrical about the double bond and free of vinyl groups and these data are thus confirmatory of the formation of the above depicted symmetrical two-to-one adduct.

The reaction of hexamethylenetetramine and 3,4-dichlorobutene-1 to form the two-to-one quaternary ammonium adduct of this invention should advantageously be carried out in an inert organic solvent in which the reactants are substantially soluble and the product is substantially insoluble. Suitable solvents are hydrocarbon and chlorinated hydrocarbon solvents such as chloroform and perchloroethylene.

The reaction should be conducted between 0°C. and a maximum upper limit of about 130°C., the decomposition point of the two-to-one quaternary ammonium adduct. There are no necessary pressure conditions for the reaction, and the reaction can thus be carried out at sub, super or normal atmospheric pressure. However, use of super atmospheric pressure reduces substantially the reaction time.

Consequently, the only two requisite reaction parameters are that (1) the reaction be carried out in an inert organic solvent in which the product is substantially insoluble and (2) the reaction temperature be maintained at less than about 130°C. to avoid decomposition of the product.

B. Structural Characteristics of the Products

In view of the disclosure of the Wolf and Frank patents, it is unexpected and unpredictable that a two-to-one quaternary ammonium adduct is formed by the reaction of hexamethylenetetramine with 3,4-dichlorobutene-1. A number of analyses have been conducted upon the product obtain according to this invention which confirm that high yields of the two-to-one quaternary ammonium adduct are obtained by the process of this invention.

Table I on pages 5 represents a comparison of analytical data relating to the organic-ionic chlorine content of products obtained according to this invention and products obtained by varying the conditions of example 1 of the Frank patent. The data in Table I confirm that the product of this invention is a two-to-one rather than one-to-one quaternary ammonium adduct.

TABLE I

| Product and Preparation Technique | Total Chlorine Calculated | Total Chlorine Obtained | Organic Chlorine Calculated On Total Chlorine Calculated | Organic Chlorine Calculated On Total Chlorine Obtained |
|---|---|---|---|---|
| Repetition of Example 1 of Frank patent | 26.6% | 24.7% | 13.3% | 12.4% |
| Repetition of Example 1 of Frank patent with large excess of 1,4-dichlorobutene-2 | 26.6% | 25.9% | 13.3% | 13.0% |
| Repetition of Example 1 of Frank patent using extended reflux and large excess of 1,4-dichlorobutene-2 | 26.6% | 25.7% | 13.3% | 12.9% |
| Procedure according to this invention using 3,4-dichlorobutene-1 | 17.5% | 17.7% | 0 | 0 |
| Procedure according to this invention using 3,4-dichlorobutene-1 | 17.5% | 17.1% | 0 | 0 |
| Procedure according to this invention using 3,4-dichlorobutene-1 | 17.5% | 17.1% | 0 | 0 |
| Procedure according to this invention using 3,4-dichlorobutene-1 | 17.5% | 16.1% | 0 | 0 |

| Product and Preparation Technique | Organic Chlorine Obtained | Ionic Chlorine Calculated On Total Chlorine Calculated | Ionic Chlorine Calculated On Total Chlorine Obtained | Ionic Chlorine Obtained |
|---|---|---|---|---|
| Repetition of Example 1 of Frank patent | 10.8% | 13.3% | 12.4% | 13.9% |
| Repetition of Example 1 of Frank patent with large excess of 1,4-dichlorobutene-2 | 11.8% | 13.3% | 13.0% | 14.1% |
| Repetition of Example 1 of Frank patent using extended reflux and large excess of 1,4-dichlorobutene-2 | 11.7% | 13.3% | 12.9% | 14.0% |
| Procedure according to this invention using 3,4-dichlorobutene-1 | 0.4% | 17.5% | 17.7% | 17.3% |
| Procedure according to this invention using 3,4-dichlorobutene-1 | 2.1% | 17.5% | 17.1% | 15.0% |
| Procedure according to this invention using 3,4-dichlorobutene-1 | 1.0% | 17.5% | 17.1% | 16.1% |
| Procedure according to this invention using | | | | |

TABLE I-continued

| Product and Preparation Technique | Total Chlorine Calculated | Total Chlorine Obtained | Organic Chlorine Calculated On Total Chlorine Calculated | Organic Chlorine Calculated On Total Chlorine Obtained |
|---|---|---|---|---|
| 3,4-dichlorobutene-1 | 0.2% | 17.5% | 16.1% | 15.9% |

Additionally, determinations of the percent nitrogen in the product of this invention confirms that the two-to-one quaternary ammonium adduct is formd. Table II is a comparison of the percentages of nitrogen calculated and obtained for the product of this invention and the one-to-one quaternary ammonium adduct formed according to example 1 of the Frank patent.

TABLE II

|  | Nitrogen Calculated | Nitrogen Obtained |
|---|---|---|
| Repetition of Example 1 of the Frank patent | 21.1% | 22.6% |
| Procedure according to this invention using 3,4-dichlorobutene-1 | 27.6% | 27.8% |

Nuclear magnetic resonance and infrared analysis confirm that the product of this invention is the two-to-one quaternary ammonium adduct, presumably prepared according to the rearrangement mechanism outlined hereinabove. These data indicate (1) the absence of monosubstituted ethylene or vinyl groups and (2) high symmetry about the double bond; both of these structural aspects confirm that the final product is completely or almost completely made up of the symmetrical two-to-one adduct. However, the presence of insignificant amounts of a one-to-one adduct cannot be conclusively ruled out by these techniques.

As a result of the elemental analysis for organic chlorine, ionic chlorine and nitrogen and the nuclear magnetic resonance and infrared analysis, it has been determined that the product made according to this invention is almost completely, if not completely, made up of the symmetrical two-to-one quaternary ammonium adduct of 3,4-dichlorobutene-1 with hexamethylenetetramine, i.e. 1,1'-(but-2-enylene) bis(3,5,7-triaza-1-azoniaadamantane chloride).

C. Antimicrobial Activity of the Product

The two-to-one quaternary ammonium adduct of hexamethylenetetramine and 3,4-dichlorobutene-1 is a more active antimicrobial agent than either of the one-to-one quaternary ammonium adducts of Wolf and Frank. The higher activity is due to the fact that there are two hexamethylenetetramine nuclei in the product of this invention, both of which upon decomposition liberate formaldehyde. Consequently, the same amount by weight of the two-to-one quaternary ammonium adduct of this invention is more active as an antimicrobial agent than the same amount by weight of the one-to-one adducts of Frank and Wolf. In this sense more active means that assuming that (1) the amount of quaternary ammonium adduct used and (2) the rate of formaldehyde release are the same, the antimicrobial activity of the two-to-one quaternary ammonium adduct of this invention will be more persistent as the two-to-one adduct will release formaldehyde for a significantly longer period of time. Consequently the same amount of the two-to-one quaternary ammonium adduct of this invention is capable of controlling larger numbers of microorganisms.

Additionally, the two-to-one adduct formed from hexamethylenetetramine and 3,4-dichlorobutene-1 according to this invention is less toxic than either the Frank or Wolf one-to-one adducts. For instance, data comparing the toxicological character of the two-to-one adduct of this invention to that of both the one-to-one adduct of example 1 of Frank and the one-to-one adduct prepared from hexamethylenetetramine and 1,3-dichloropropene according to Wolf (available commercially as Dowicil 100 and 200) indicate the two-to-one adduct to have a significantly superior toxicological profile.

Table III shows these comparative data for both acute dermal and acute oral $LD_{50}$ tests. Both the acute oral $LD_{50}$ and acute dermal $LD_{50}$ tests were run in accordance with standard, accepted protocols.

TABLE III

| Product | Acute Oral $LD_{50}$ | Acute Dermal $LD_{50}$ |
|---|---|---|
| One-to-one adduct of hexamethylenetetramine and 1,-3-dichloropropene | 745 mg/kg* | 540 mg/kg** |
| One-to-one adduct of hexamethylenetetramine and 1,4-dichlorobutene-2 | 1.6 gm/kg | 2.0 gm/kg |
| Two-to-one adduct of hexamethylenetetramine and 3,4-dichlorobutene-1 | 3.4 gm/kg | 8.0 gm/kg |

*Data available from Dow Chemical on Dowicil 100.
**Data available from Dow Chemical on Dowicil 200.

From the data in Table III, it is apparent that the two-to-one adduct of this invention is markedly superior from a toxicological standpoint than the prior art one-to-one adducts.

D. The Antimicrobial Uses of the Product

The two-to-one quaternary ammonium adduct of this invention is a water-soluble, non-metallic, non-phenolic antimicrobial agent effective against a broad spectrum of gram positive and gram negative microorganisms. The two-to-one quaternary ammonium adduct of this invention is particularly useful as an antimicrobial agent in a wide variety of water-based systems such as latex paints, resin emulsions, joint cement, adhesives, dispersed pigments and dyes, and other similar aqueous compositions.

The two-to-one quaternary ammonium adduct of this invention is useful in the preparation and storage of systems susceptible to deterioration by microorganisms such as the common forms of bacteria. The exact concentration of the adduct during use is dependent upon a number of factors including duration of storage, temperature of storage, etc. However, concentrations in the range of 0.05 to 0.20% based upon the weight of the composition have been found to be generally effective. It should be noted, however, that the minimal inhibitory concentrations vis-a-vis the common bacteria are much less than this suggested range for use under commercial conditions.

SPECIFIC EMBODIMENTS OF THE INVENTION

The following Examples are non-limitative embodiments of the invention and are included merely as specific examplification of the invention

EXAMPLE 1

To a 1 liter flask equipped with stirrer, thermometer and reflux condenser is charged:

| | |
|---|---|
| chloroform | 600 mls |
| hexamethylenetetramine | 70 grams |
| 3,4 dichlorobutene-1 | 125 grams |
| sodium carbonate | 10 grams |

The reaction mass is refluxed for 30 hours and then cooled to room temperature and filtered. The filter cake is washed three times with a total of 750 mls of chloroform and then allowed to air dry. The theoretical calculated yield is 111 grams while the actual weight obtained is 108 grams.

EXAMPLE 2

To a 2 liter stirring autoclave the following charge is added:

| | |
|---|---|
| chloroform | 1,020 mls |
| hexamethylenetetramine | 119 grams |
| butylated hydroxy toluene | 0.184 grams |
| 3,4 dichlorobutene-1 | 212.5 grams |
| sodium carbonate | 8.5 grams |

The reaction is maintained at 80°C for a period of 18 hours with a maximum generated pressure of 12 psi. At the end of the reaction period, the mixture is cooled and filtered. The filter cake is then washed with 350 ml increments of chloroform three times and then placed in a vacuum oven at 40° to constant weight. The theoretical calculated yield is 180.5 grams while the actual yield obtained is 166 grams.

EXAMPLE 3

To a 1 liter flask equipped with stirrer, thermometer and reflux condenser is charged:

| | |
|---|---|
| perchloroethylene | 600 mls |
| 3,4 dichlorobutene-1 | 125 grams |
| hexamethylenetetramine | 70 grams |
| sodium carbonate | 10 grams |

The reaction is heated at 75°C for 25 hours. Product mix is cooled and then filtered. Filter cake is washed 4 times with 250 ml increments of perchloroethylene and then air dried. The theoretical calculated yield is 111 grams and the actual yield obtained is 104 grams.

EXAMPLE 4

The product of this invention had demonstrated especially high antibacterial performance in the preservation of latex and emulsion based paints. The following is a description of a notable paint formulation.

To a 1 gallon stainless steel beaker, equipped with a shear type agitator, the following ingredients are charged in sequence:

| | |
|---|---|
| water | 849 grams |
| anionic dispersant | 18 grams |
| potassium tripolyphosphate | 4 ½ grams |
| nonionic surfactant | 6 grams |
| defoamer | 6 grams |
| ethylene glycol | 60 grams |

| | |
|---|---|
| two-to-one adduct of this invention | 3.6 grams |
| titanium dioxide | 750 grams |
| pigment extender | 450 grams |

In a separate 100 ml beaker, the following premix is prepared:

| | |
|---|---|
| hydroxyethylcellulose | 9 grams |
| coupling solvent | 24 grams |

This premix is then added to the above with agitation such that excessive air is not incorporated. To the above prepared combination is added 1,401 grams of a vinyl acrylic resin emulsion, and mixed for a period of 10 minutes.

The resulting paint prepared above was examined for antibacterial properties by inoculating a portion with approximately $10^8$ organisms per ml *Pseudomonas aeruginosa*. Paint samples returned to sterility within 24 hours of inoculation and maintained the same degree of preservation for periods in excess of 9 months, at which time the testing was discontinued. The addition of test compound preserved the paint system against attack from microbial contamination and thereby maintained the viscosity, stability and performance characteristics of the paint.

EXAMPLE 5

The following is a formulation for an oil-water hair dressing emulsion:

| | |
|---|---|
| Part A | |
| Petrolatum | 5.5% |
| Mineral Oil | 35.0% |
| Bees Wax | 4.5% |
| Lanolin Derivative Emulsifier | 4.0% |
| Nonionic Emulsifier | 2.0% |
| Part B | |
| Water | 48.3% |
| Part C | |
| Two-to-one adduct of this invention | 0.2% |

Part A is heated to 75°C and Part B is heated to 70°C. The test compound (Part C) is dissolved in Part B and the resulting solution added to Part A with good agitation. The mixture was perfumed at 45°C and agitated until cold.

The composition prepared above was tested for microbial stability for a period of 6 months and after 6 month at 35°C. Inoculation with bacterial cultures at this point showed the material still resistant to bacterial contamination.

We claim:

1. A method for preparing the two-to-one quaternary ammonium adduct of hexamethylenetetramine and 3,4-dichlorobutene-1 which comprises reacting 3,4-dichlorobutene-1 with hexamethylenetetramine at a temperature of less than about 130°C. in an inert organic solvent in which the adduct is substantially insoluble.

2. A composition consisting essentially of the two-to-one quaternary ammonium adduct of hexamethylenetetramine and 3,4-dichlorobutene-1.

* * * * *